US012644938B2

(12) United States Patent
Hai et al.

(10) Patent No.: US 12,644,938 B2
(45) Date of Patent: Jun. 2, 2026

(54) IMPLANTABLE SENSOR FOR USE WITH MAGNETIC RESONANCE IMAGING

(71) Applicant: Wisconsin Alumni Research Foundation, Madison, WI (US)

(72) Inventors: Aviad Hai, Madison, WI (US); Suyash Bhatt, Monona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 18/765,839

(22) Filed: Jul. 8, 2024

(65) Prior Publication Data

US 2025/0291009 A1 Sep. 18, 2025

Related U.S. Application Data

(60) Provisional application No. 63/566,249, filed on Mar. 16, 2024.

(51) Int. Cl.
*A61B 5/00* (2006.01)
*A61B 5/055* (2006.01)
*G01R 33/34* (2006.01)

(52) U.S. Cl.
CPC ...... *G01R 33/34084* (2013.01); *A61B 5/0036* (2018.08); *A61B 5/055* (2013.01); *A61B 5/686* (2013.01)

(58) Field of Classification Search
CPC . G01R 33/34084; A61B 5/0036; A61B 5/055; A61B 5/686
See application file for complete search history.

(56) References Cited

U.S. PATENT DOCUMENTS

| | | | | |
|---|---|---|---|---|
| 2005/0104577 A1* | 5/2005 | Matei | ................. | A61N 1/37288 |
| | | | | 324/207.13 |
| 2018/0279924 A1* | 10/2018 | Kuhn | .................. | A61B 5/1459 |
| 2020/0046224 A1* | 2/2020 | Jasanoff | .................. | A61B 5/05 |
| 2021/0076938 A1* | 3/2021 | Gerlach | ................. | A61B 18/14 |
| 2022/0407360 A1* | 12/2022 | Chiao | .................... | H02J 50/12 |

OTHER PUBLICATIONS

T. Li, X. Jin, L Tang, W.-L Lv, M.-M. Xiao, Z.-Y. Zhang, C. Gao, G.-J. Zhang, Receptor-mediated field effect transistor biosensor for real-time monitoring of glutamate release from primary hippocampal neurons, Anal. Chem. 91 (2019) 8229-8236 (Year: 2019).*
Suyash Bhatt et.al.; Wireless in vivo recording of cortical activity by an ion-sensitive field effect transistor. Sensors and Actuators B: Chemical 382 (2023): 133549. pp 1-11 (Year: 2023).*
(Continued)

*Primary Examiner* — Alexei Bykhovski
(74) *Attorney, Agent, or Firm* — Boyle Fredrickson, S.C.

(57) ABSTRACT

A microscale resonator tuned to an MRI Larmor frequency during MRI imaging may be implanted in tissue to monitor ion concentration using the MRI imaging system detecting changes in the resonant frequency of the microscale resonator caused by coupling to tissue ions. The application of a radiofrequency electrical field to the microscale resonator may permit ablation of local tissue.

19 Claims, 3 Drawing Sheets

(56) References Cited

OTHER PUBLICATIONS

Aviad Hai et.al.; "Wireless resonant circuits for the minimally invasive sensing of biophysical processes in magnetic resonance imaging." Nature biomedical engineering 3, No. 1 (2019): pp. 69-78. US.

Razvan Ciocan et. al.; "MRI contrast using solid-state, B1-distorting, microelectromechanical systems (MEMS) microresonant devices (MRDs)." Magnetic Resonance in Medicine: An Official Journal of the International Society for Magnetic Resonance in Medicine 61, No. 4 (2009): pp. 860-866. US.

Suyash Bhatt et.al.; "Wireless in vivo recording of cortical activity by an ion-sensitive field effect transistor." Sensors and Actuators B: Chemical 382 (2023): 133549. pp 1-11. US.

* cited by examiner

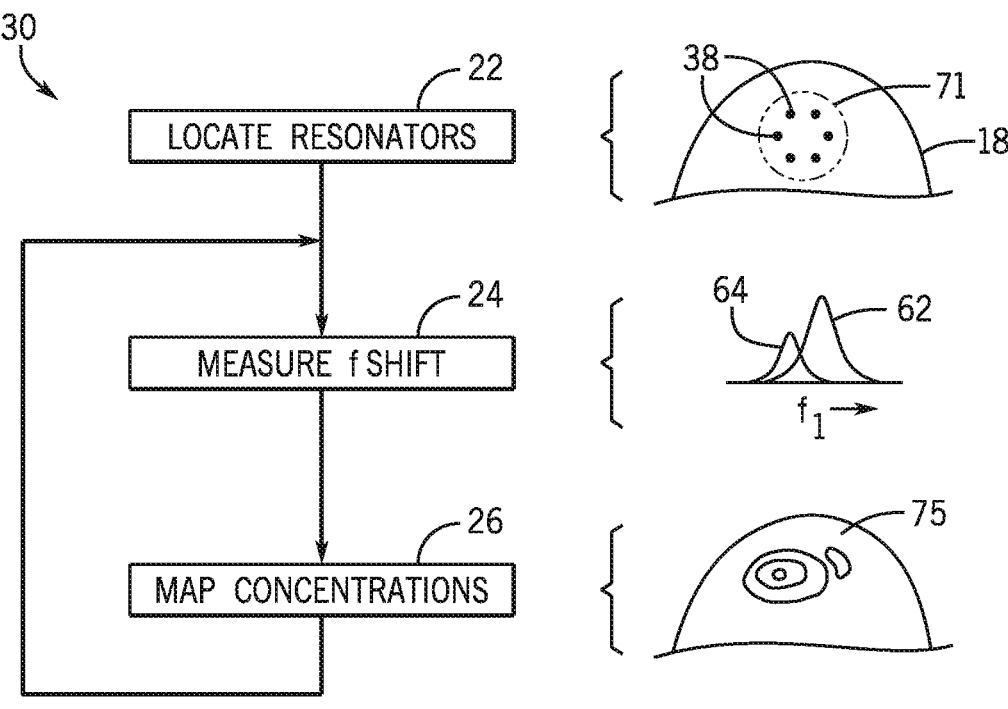
FIG. 5
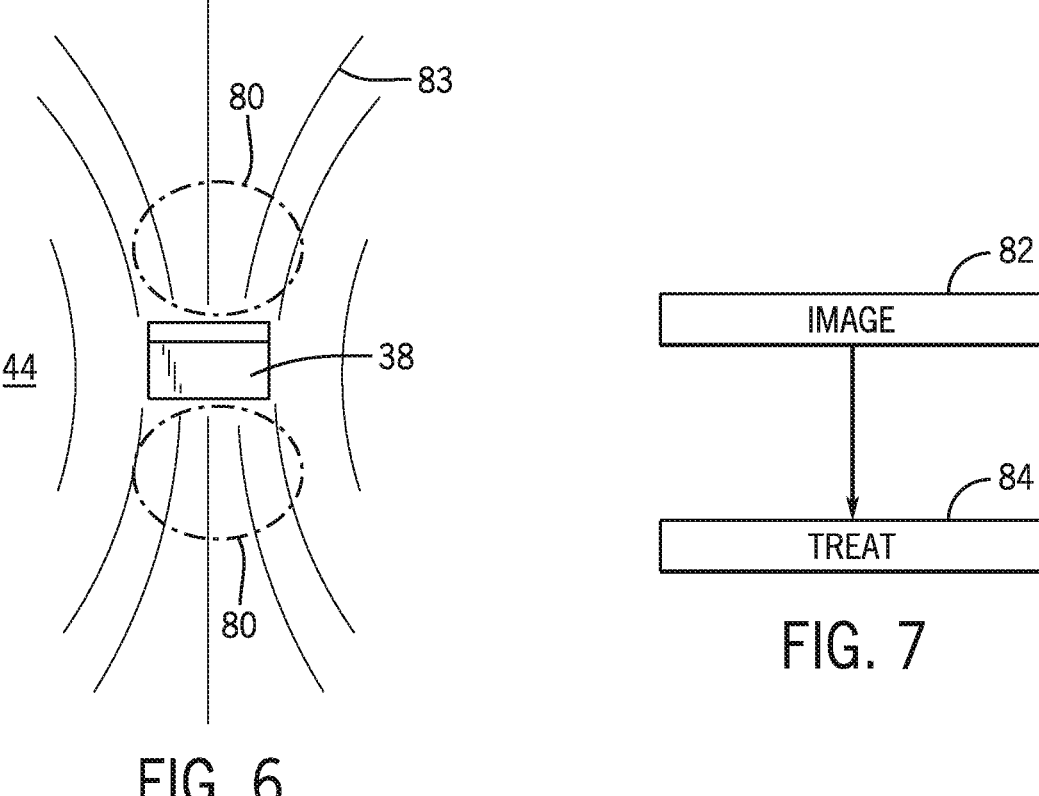
FIG. 6
FIG. 7

IMPLANTABLE SENSOR FOR USE WITH MAGNETIC RESONANCE IMAGING

CROSS REFERENCE TO RELATED APPLICATION

This application claims the benefit of U.S. provisional application 63/566,249 filed Mar. 16, 2024, and hereby incorporated by reference.

STATEMENT REGARDING FEDERALLY SPONSORED RESEARCH OR DEVELOPMENT

This invention was made with government support under NS122605 awarded by the National Institutes of Health and under N00014-22-1-2371 and N00014-23-1-2006 awarded by the NAVY/ONR. The government has certain rights in the invention.

BACKGROUND OF THE INVENTION

The present invention relates generally in vivo sensors and in particular to an implantable in vivo sensor that can be interrogated using MRI imaging equipment.

Glioblastoma multiforme (GBM) remains the most common and the most aggressive form of brain cancer especially in older adults, having a short average survival time and poor prognosis, with reoccurrence in 90% of cases. Despite advancements in both established clinical paradigms for GBM treatment such as radiation, chemotherapy, and surgical resection, and more recent experimental therapies such as immunological disruption and application of tumor treating fields, early detection remains paramount for more effective therapy leading to increased long-term survival rates.

SUMMARY OF THE INVENTION

The present invention provides a biocompatible, implantable sensor that in one example embodiment, can monitor reoccurrence of GBM by tracking concentrations of extracellular potassium ions [K+]. These ions modify a passive circuit that can be imaged and interrogated by standard MRI systems. More generally, the sensor can be used for a variety of similar detection tasks, for example, monitoring glutamate for assessing traumatic brain injury, and holds promise for local area ablation.

In one embodiment, the invention provides a method of in vivo tissue monitoring and/or treatment using an implantable circuit assembly providing an interconnected electrical inductive element and an electrical capacitive element cooperating to produce an electrically resonant circuit having a natural resonant frequency within a range of 60 MHz to 300 MHz in the presence of surrounding tissue. The implanted circuit assembly can be imaged with an MRI machine to detect changes in the natural resonant frequency of the circuit assembly and these latter changes used to determine a measure of ion concentrations in the surrounding tissue.

It is thus a feature of at least one embodiment of the invention to provide the ability to monitor local tissue conditions deeply within tissue using implantable sensors readable with MRI equipment.

The injectable circuit assembly may have a volume that will not fit within a 0.05 mm cube and a volume that will fit within a 2 mm cube.

It is thus a feature of at least one embodiment of the invention to provide a circuit that is both small enough to be readily implanted and retained in the tissue and yet which has sufficient area to interact with ions within the tissue to promote appreciable detuning.

The electrical inductive element may be a pancake coil providing a substantially planar spiral conductor.

It is thus a feature of at least one embodiment of the invention to provide an inductor that can be readily fabricated, for example but not limited to, using photolithographic techniques, and that provides a broad coupling with local tissue.

A surface of the exposed injectable circuit assembly may be functionalized to promote attraction of predetermined ions, for example, potassium ions overexpressed in GBM or glutamate anions associated with traumatic brain injury or secondary injury.

The method may include inserting the circuit assembly into a hypodermic needle for introduction into tissue through a hypodermic needle.

It is thus a feature of at least one embodiment of the invention to provide a circuit assembly that can be readily managed using a hypodermic needle for deep tissue insertion.

The method may attach a vane element to the injectable circuit assembly promoting a predetermined orientation of the injectable circuit, for example, aligned with the $B_0$ field of the MRI machine, when passing through a hypodermic needle.

It is thus a feature of at least one embodiment of the invention to provide control of the circuit orientation promoting sensitivity during MRI imaging.

The method may insert multiple circuit assemblies into the tissue and use the MRI machine to both spatially map the location of the multiple circuit assemblies and to output an image of ion concentration as a function of location. Such mapping can be extended over time.

It is thus a feature of at least one embodiment of the invention to provide for an improved spatial understanding of tissue ion concentrations, for example, in the region of an excised tumor or brain injury and how they change with time.

The method may include the step of applying a radiofrequency field to the circuit assembly to ablate local tissue.

It is thus a feature of at least one object of the invention to permit both monitoring and treatment of tissue using embedded circuit elements.

These particular objects and advantages may apply to only some embodiments falling within the claims and thus do not define the scope of the invention.

BRIEF DESCRIPTION OF THE DRAWINGS

FIG. 5 is a flowchart of a program executable on the MRI system of FIG. 1 for concentration mapping of an arbitrarily arrayed set of implantable resonators;

FIG. 6 is a phantom view of tissue about an implantable resonator showing the concentration of electrical field lines for ablation; and FIG. 7 is a flowchart showing a successive use of different imaging protocols to image/measure ion concentration and ablate tissue.

DETAILED DESCRIPTION OF THE PREFERRED EMBODIMENT

Figures 1, 2A, 2B:
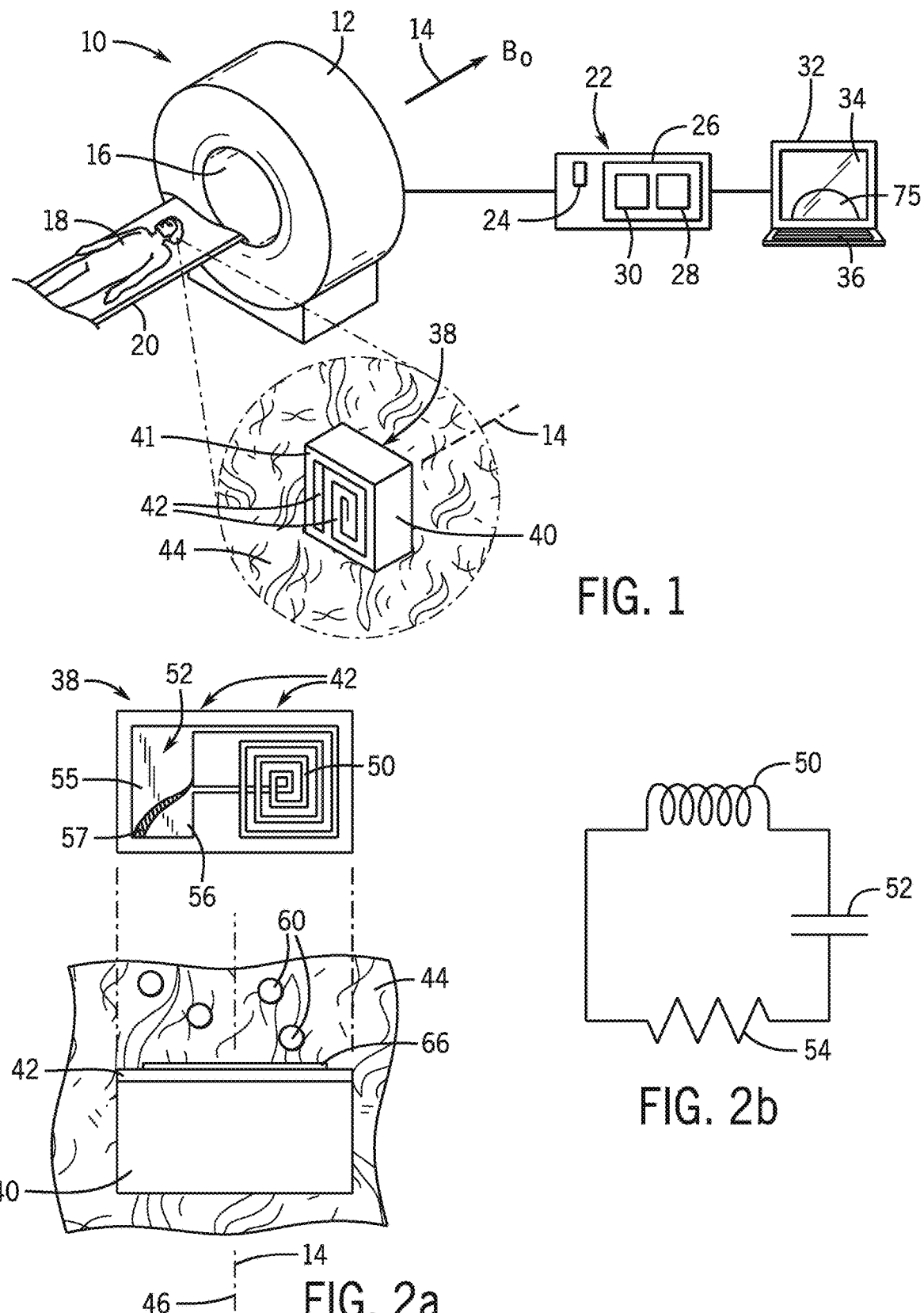
FIG. 1 is a simplified block diagram of an MRI system suitable for practice of the present invention showing the implantable resonator in an expanded detail view.
FIGS. 2a and 2b are respectively a top plan view in partial cutaway of the implantable resonator positioned in alignment over an expanded elevational cross-section of the implantable resonator of FIG. 1 and a schematic representation of the same.

Referring now to FIG. 1, a magnetic resonance imaging (MRI) system 10 suitable for use with the present invention may provide a scanner 12 incorporating a magnet assembly. The magnet assembly produces a static magnetic field ($B_0$) oriented along a principal field axis 14 typically aligned with the axis of a bore 16 through the scanner 12. The bore 16 provides an opening into which a patient 18 may be received supported on a patient table 20. In useful examples, the magnet assembly will provide a superconducting electromagnetic solenoid wound about the field axis 14 producing a static magnetic field, for example, from 0.5 to 7 Teslas.

As is generally understood in the art, the scanner 12 will also include gradient coils for modifying the static magnetic field ($B_0$) and radiofrequency coils for exciting tissue protons of the patient 18 into magnetic resonance. This magnetic resonance will occur at a Larmor frequency dependent on the field strength of the magnet assembly and typically ranging from 60 MHz to 300 MHz.

The components of the scanner 12 may be associated with electronic circuitry (for example, gradient amplifiers and radiofrequency amplifiers) communicating with an electronic computer 22 or similar control circuit. The electronic computer 22 may provide one or more processors 24 connecting to interface lines to the scanner 12 and with a stored memory 26 holding an imaging program 28 providing for the acquisition of MRI data as is understood in the art. The computer 22 may also include program 30 assisting in the use of the present invention and as will be discussed in more detail below.

A user terminal 32 providing, for example, a graphic display 34 for displaying MRI images augmented according to the present invention and interface input devices such as a keyboard 36 mouse trackball or the like, may communicate with the computer 22 for receiving data there from and providing control instructions thereto.

The patient 18, prior to scanning, may receive one or more implantable passive circuit assemblies 38. These circuit assemblies 38 may be inserted into tissue during surgery, for example, manually placed in an open cavity with forceps or the like, or injected with a hypodermic needle as will be discussed below. In a nonlimiting example, the circuit assemblies 38 may be distributed in the area of an excised GBM tumor for monitoring and possible treatment of brain tissue after surgery or may be located in a region of brain injury to monitor secondary injury.

The implantable passive circuit assemblies 38 are desirably sufficiently large to interact with the tissue and to provide a signal that can be interrogated using the MRI system 10 and yet sufficiently compact to be retained in the tissue without tissue injury and in some cases to be conducted through a hypodermic needle for insertion into the tissue. For this purpose, generally the circuit assemblies 38 will have a volume that will not fit within a 0.05 mm cube but will fit within a 2 mm cube. The outer surfaces of the circuit assemblies 38 will be biocompatible, for example, using relatively inert materials such as gold, glass, titanium, or the like.

In one embodiment, the passive circuit assembly 38 may be constructed, for example, using photolithographic techniques, on an inert substrate 40 such as glass. The substrate 40 may present a planar surface 41 to surrounding tissue on which circuit components 42 are deposited to be exposed to the surrounding tissue 44. In practice, multiple passive circuit assemblies 38 may be fabricated on a single substrate that is then scored and broken into individual passive circuit assemblies 38. In some embodiments, a spaced array of passive circuit assemblies 38 may also be constructed and used without separation, either rigidly attached to each other or attached together by means of a flexible network or mesh, to provide for a desired spacing or dispersal within tissue.

Referring now to FIG. 2, the circuit components 42 will include an inductive element 50 and a capacitive element 52 connected together in a series resonant circuit and experiencing inherent distributed resistance 54 from the conductive materials of the inductive element 50 and capacitive element 52 and their interconnections. The resistive element 54 is desirably minimized so as to provide a high Q resonant circuit with a Q of above 10 or more.

The capacitive element 52 may provide for an upper plate 55 and a lower plate 56 of a conductive material such as gold or titanium in close proximity separated by a dielectric material or insulator 57. The upper plate 55 and lower plate 56 are generally parallel to the planar surface 41 on which they are fabricated.

The inductive element 50 may be a so-called pancake or fingerprint coil providing for a spiral of conductive material confined largely to the plane of the surface 41 thus presenting a broad area toward the tissue that will be most sensitive to magnetic fields oriented along the surface normal 46. The surface normal 46 and hence the normal to the plane of the inductive element 50 is desirably closely aligned with axis 14 of the MRI scanner 12 to provide improved coupling between an inductive element of the circuit components 42 and the field aligned with axis 14.

In this regard, the particular values of the capacitive element 52 and the inductive element 50 are selected to provide a natural resonant frequency of the resulting resonant circuit comparable to the Larmor frequency of the MRI scanner 12, specifically between 60 MHz and 300 MHz.

Notably the implantable passive circuit assembly 38 may employ only passive components, excluding elements such as transistors, photodiodes, or the like, greatly simplifying its fabrication, reducing its cost, and limiting the necessary power levels for interrogation of the circuit assembly 38 as a sensor by the MRI system 10.

Figure 3:
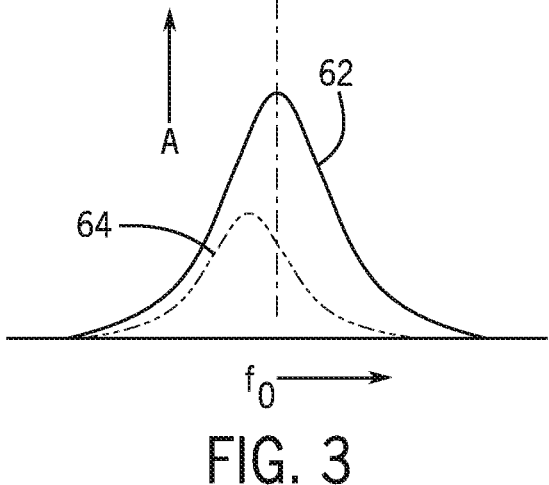
FIG. 3 is a plot of frequency versus amplitude showing the effect of resonant frequency shifting on apparent pixel brightness.

Referring also to FIG. 3, when the circuit assembly 38 is embedded in tissue 44, the inductive element 50 will inductively couple to dielectric material of the tissue 44 as affected by a concentration of ions 60, for example, potassium ions [K+] or glutamate anions. Changes in the dielectric of the tissue 44 alter the tuning of the resonant circuit of the circuit assembly 38, for example, from a first frequency response 62 having a peak or center frequency of $f_0$ closely matching the Larmor frequency of the MRI system 10 to a second detuned frequency response 64 normally having a lower Q and shifted downward in frequency with increased ionic concentrations. The effect of this detuning will be to change the apparent intensity of a voxel or multiple voxels in the vicinity of the passive circuit assembly 38 in a produced MRI image. MRI spectrographic methods may also be used to characterize this frequency shift. These changes in signal intensity or frequency shift may be mapped to ion concentrations, for example, using an empirically derived lookup table, function, or the like and expressed quantitatively or qualitatively on an output to the user terminal 32 as will be discussed below.

Referring again to FIG. 2a, in some embodiments, greater selectivity or sensitivity to tissue ions may be provided by functionalizing the surface 41 to promote accumulation of the ions of interest. In one example, the surface 41 may be functionalized as taught by T. Li, X. Jin, L Tang, W.-L Lv, M.-M. Xiao, Z.-Y. Zhang, C. Gao, G.-J. Zhang, Receptor-mediated field effect transistor biosensor for real-time monitoring of glutamate release from primary hippocampal neurons, Anal. Chem. 91 (2019) 8229-8236, https://doi.org/10.1021/acs.analchem.9b00832, hereby incorporated by reference.

Figure 4:
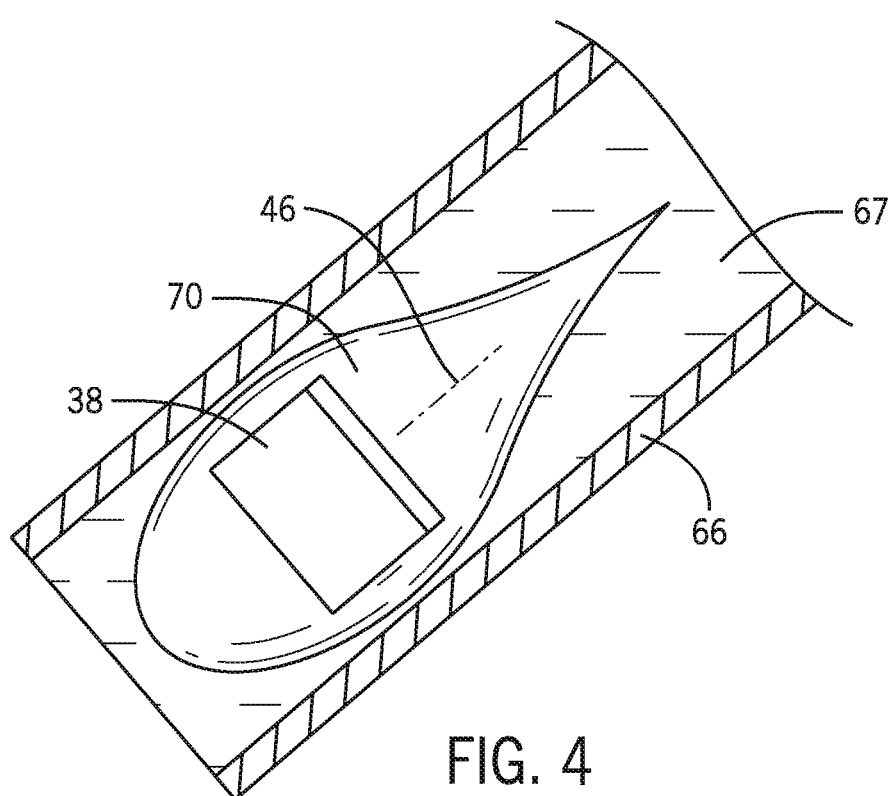
FIG. 4 is a cross-sectional view through a distal tip of a hypodermic needle used for implantation of the implantable resonator and showing an orienting vane structure.

Referring now to FIG. 4, a convenient delivery system for the circuit assembly 38 may employ a hypodermic needle 66 connected to a syringe (not shown), the latter containing a saline solution 67 or the like to propel the contained circuit assembly 38 through the hypodermic needle 66 into tissue at a desired location. In order to provide a controlled orientation of the circuit assembly 38 as it passes through the hypodermic needle 66, the circuit assembly 38 may be embedded in a vane material 70, sized and shaped to orient the circuit assembly 38 in a predetermined direction with respect to the axis of the needle 66, either by mechanical interference with the internal diameter of the hypodermic needle 66 or through alignment with fluid flow during the injection process. In one example, the vane material 70 may be a partially solidified hydrogel material into which the circuit assembly 38 is embedded, for example, so as to orient the surface normal 46 of the circuit assembly along the axis of the needle 66. Appropriate angulation of a hypodermic needle 66 may then align the surface normal with the static magnetic field $B_0$.

The vane material 70 may also serve to stabilize the circuit assembly 38 in the tissue and may be selected to be absorbed and dissipated after a period of time. In some embodiments, the vane material 70 may be permeable or selectively permeable to ion species of interest.

Referring now to FIG. 5, the program 30 may, in conjunction with program 28, operate the MRI system 10 to process the imaged voxel signals in the regions around the circuit assembly 38 to extract and output ion concentrations, for example, mapping changes in signal intensity or frequency peak to ion concentrations using empirically derived formulas. In one embodiment, depicted in FIG. 5, multiple circuit assemblies 38 may be deposited, as indicated by process block 72, within a volume of interest 71 within the tissue of the patient 18. This volume of interest 71, as discussed above, may be a region of surgical excision of a tumor or an injured region where it is desired to monitor that tissue and possibly provide future treatment. After such deposition as indicated by process block 72, an MRI image may be obtained of the volume of interest 71 to identify the locations in three dimensions of the deposited circuit assemblies 38.

A similar or separate imaging protocol may be adopted per process block 74 to then measure the ion concentrations at each region to link an ion concentration to a spatial location. Knowledge of the locations and concentrations allow concentration zones to be described providing a mapping 75 per process block 76 of any changes in ion concentration that suggest a recurrence of a tumor or other neurological defect.

This mapping 75 may be displayed in conjunction with other MRI imaging data (for example, superimposed on a conventional MRI image) for context on display 34 (shown in FIG. 1). Process blocks 74 and 76 may be repeated over a span of time to provide, for example, an animated depiction of the evolution of ion concentrations.

Referring to FIG. 6, the presence of embedded circuit assemblies 38 is expected to interact with the radiofrequency fields 83 of the MRI system 10 to potentially produce areas of concentrated electrical fields 80 providing for non-thermal ablation of tissue in those regions. In such a situation, as indicated in FIG. 7, the MRI system 10 may first conduct an imaging per process block 82, for example, implementing process blocks 72-76 and subsequently may implement a different protocol 84 intended to promote the concentrated electrical fields 80 for the purposes of ablation.

When multiple circuit assemblies 38 are implanted into tissue, they may each be independent of each other, or they may be assembled together or loosely interconnected in an array. Pairs of connected circuit assemblies 38 may be employed, for example, so that one circuit assembly 38 provides a measure of ion concentrations and the other circuit assembly 38 provides a decoupled circuit assembly 38 offering a reference signal. Alternatively, or in addition, pairs of circuit elements may be interconnected at different orientations to reduce angular sensitivity in the received signals.

The term "passive circuit" as used herein refers to circuits composed of electrical components that consume energy but do not switch or produce energy, and generally include linear components showing a linear relationship between voltage and current such as inductors, resistors, and capacitors and excluding power sources, transistors, and the like.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A method of in vivo tissue monitoring comprising:
(a) implanting within the tissue at least one passive circuit assembly providing biocompatible outer surfaces and including an interconnected electrical inductive element and an electrical capacitive element cooperating to produce an electrically resonant circuit having a natural resonant frequency within a range 60 MHz to 300 MHz in a presence of a surrounding tissue;
(b) imaging the tissue with the at least one passive circuit assembly with an MRI machine providing an axis, defining a $B_o$ field, to detect changes in the natural resonant frequency of the at least one passive circuit assembly; and
(c) determining a measure of ion concentrations in a dielectric material of the surrounding tissue based on the changes in natural resonant frequency.

2. The method of claim 1 wherein the at least one passive circuit assembly has a volume that will not fit within a 0.05 mm cube and a volume that will fit within a 2 mm cube.

3. The method of claim 1 wherein the electrical inductive element is a pancake coil providing a substantially planar spiral conductor.

4. The method of claim 1 including functionalizing a surface of the at least one passive circuit assembly exposed to the tissue to promote attraction of predetermined ions.

5. The method of claim 4 wherein the predetermined ions are selected from the group consisting of glutamate ions and potassium ions.

6. The method of claim 1 wherein (a) includes inserting the at least one passive circuit assembly into a hypodermic needle for introduction into the tissue through the hypodermic needle.

7. A method of in vivo tissue monitoring comprising:
(a) implanting within the tissue at least one circuit assembly providing biocompatible outer surfaces and including an interconnected electrical inductive element and an electrical capacitive element cooperating to produce an electrically resonant circuit having a natural resonant frequency within a range 60 MHz to 300 MHz in a presence of a surrounding tissue;
(b) imaging the tissue with the implanted at least one circuit assembly with an MRI machine providing an axis, defining a Bo field, to detect changes in the natural resonant frequency of the at least one circuit assembly; and
(c) determining a measure of ion concentrations in a dielectric material of the surrounding tissue based on the changes in natural resonant frequency;
wherein (a) includes inserting the at least one circuit assembly into a hypodermic needle for introduction into the tissue through the hypodermic needle; and
further including attaching a vane element to the at least one circuit assembly promoting a predetermined orientation of the at least one circuit assembly when passing through the hypodermic needle.

8. The method of claim 1 further including the step of aligning an axis of the electrical inductive element for greatest sensitivity to variations in a magnetic field along the axis.

9. The method of claim 1 wherein the at least one passive circuit assembly is multiple circuit assemblies and including the step of spatially mapping locations of the multiple circuit assemblies to output an image of ion concentration as a function of location.

10. The method of claim 1 further including the step of repeating (b) and (c) to output an indication of ion concentration change as a function of time.

11. The method of claim 1 further including the step applying a radiofrequency field to the at least one passive circuit assembly to ablate local tissue.

12. An MRI resonator comprising:
an injectable passive circuit assembly providing biocompatible outer surfaces, the injectable passive circuit assembly including:
(a) an insulating substrate;
(b) an electrical inductive element deposited on the substrate and having an area greater than $0.05 \text{ mm}^2$ and less than $2 \text{ mm}^2$ adjacent to surrounding tissue when inserted in tissue;
(c) an electrical capacitive element deposited on the substrate and communicating with the electrical inductive element and operating therewith to produce an electrically resonant circuit having a natural resonant frequency within a range of 60 MHz to 300 MHz in a presence of the surrounding tissue; and
wherein the injectable passive circuit assembly is configured to couple to a dielectric material of the surrounding tissue to change its natural resonant frequency depending on ion concentrations in the dielectric material of the surrounding tissue.

13. The MRI resonator of claim 12 wherein the injectable passive circuit assembly has a volume that may be subtended by a 2 mm cube.

14. The MRI resonator of claim 12 wherein the electrical inductive element is a pancake coil providing a substantially planar spiral conductor.

15. The MRI resonator of claim 12 wherein a surface of the injectable passive circuit assembly exposed to the tissue is functionalized to promote attraction of predetermined ions.

16. The MRI resonator of claim 12 wherein the predetermined ions are glutamate ions.

17. The MRI resonator of claim 12 further including a vane element attached to the injectable passive circuit assembly promoting a predetermined orientation of the injectable circuit when passing through a hypodermic needle.

18. The MRI resonator of claim 17 wherein the vane element is a bioabsorbable material.

19. The MRI resonator of claim 18 wherein the vane element is a hydrogel.

* * * * *